United States Patent [19]

Dove et al.

[11] Patent Number: 5,780,236
[45] Date of Patent: Jul. 14, 1998

[54] METHOD FOR IDENTIFYING MUTANTS AND MOLECULES

[75] Inventors: William F. Dove; Alexandra Shedlovsky, both of Madison, Wis.

[73] Assignee: Wisconsin Alumni Research Foundation, Madison, Wis.

[21] Appl. No.: 751,292

[22] Filed: Nov. 18, 1996

[51] Int. Cl.$^6$ .............................. C12P 19/34; C12Q 1/68
[52] U.S. Cl. .................. 435/6; 435/91.2; 800/2; 935/77; 935/78
[58] Field of Search .................. 435/91.2; 935/77, 935/78; 800/2

[56] References Cited

U.S. PATENT DOCUMENTS 5,492,808   2/1996   de la Chapelle et al. .................. 435/6

OTHER PUBLICATIONS

Moser et al. Science 247:322–324 (Jan. 19, 1990).
Moser et al. J. Cell. Biol. 116(6):1517–1526 (Mar. 1992).
Su et al., Science 256:668–670 (May 1, 1992).
Cancer Economics, Sep. 1996, pp. 1,2 and 7.
Dietrich, et al., "Genetic Identification of Mom–1, a Major Modifier Locus affecting Min–Induced Intestinal Neoplastia in the Mouse," Cell 75:631–639 (1993).
Friedrich, Glenn A., "Moving Beyond the Genome Projects," Nature Biotechnology 14:1234–1237 (1996).
Roush, Wade, "Biotech Finds a Growth Industry," Science 273:300–301 (1996).
Shedlovsky, et al., "Induction of Recessive Lethal Mutations in the T/t–H–2 Region of the Mouse Genome by a Ponit Mutagen," Genet. Res., Camb. 47:135–142 (1986).
Zhang, et al., "Positional Cloning of the Mouse Obese Gene and its Human Homologue," Nature 372:425–432 (1994).

Primary Examiner—Stephanie W. Zitomer
Attorney, Agent, or Firm—Quarles & Brady

[57] ABSTRACT

A method for breeding mutagenized mice that permits detection of genetic loci that can modify a known index phenotype involves crossing a mutagenized founder strain and a second strain of mice carrying an allele at a locus that confers the index phenotype. In the test generation, clusters of individuals are observed to deviate from the typical phenotype. The genetic material and molecules encoded thereby can be obtained using available methods.

9 Claims, 1 Drawing Sheet

The ICMM Method

Age (days)

METHOD FOR IDENTIFYING MUTANTS AND MOLECULES

STATEMENT REGARDING FEDERALLY SPONSORED RESEARCH OR DEVELOPMENT

This invention was made with United States government support awarded by NIH, grant numbers CA23076, CA50585, CA63677, and CA07175. The United States government has certain rights in this invention.

CROSS-REFERENCE TO RELATED APPLICATIONS

Not applicable.

BACKGROUND OF THE INVENTION

Worldwide efforts to determine the genomic DNA sequences of humans and other animals are on-going. Such efforts typically focus on obtaining sequence information from cDNAs in libraries created from RNAs of various tissues. Thus, collections of "expressed sequence tags" (ESTs) include portions of coding regions from most human genes.

Although ESTs provide useful structural information, they offer little insight into the functional relationship among genes. The functional relationship is of particular importance to determining the set of genes involved in a biological process and, subsequently, to developing pharmaceutical agents that affect one or more of the components of the biological process. See, e.g., Friedrich, G. A., "Moving Beyond the Genome Projects: Does the Future of Genomics-Based Drug Discovery Lie With the Mouse?," *Nature Biotechnology* 14:1234–1237 (1996).

Friedrich argues in favor of using model systems that mirror human physiology in determining which genes may be involved in a biological process, and suggests that the mouse is an excellent model organism for human biology in that it shares with humans most salient aspects of mammalian physiology. The genomes of mice and humans are approximately the same in size, organization, and structure. Friedrich proposes that the mouse can be developed as an effective tool for drug development. Friedrich puts forth a "radical" suggestion that there is no logical barrier hindering large-scale phenotypic screens using mice.

Friedrich proposes using an insertional mutagen in embryonic stem cells to generate random mutations in the mouse genome, then screening for a variety of predetermined phenotypes and cloning affected genes.

In particular, the physiology of, and treatments for, colon cancer are of particular biomedical interest. Colon cancer is one of the most prevalent malignancies in the Western world, with an estimated 145,000 new cases and 60,000 deaths each year in the United States alone. Genetic factors play a key role in this disease. Mutations in the human adenomatous polyposis coli (APC) gene cause a set of familial colon cancer syndromes. Mice carrying a mutation in a corresponding gene (Apc) also develop many intestinal adenomas. Heterozygotes for the Min (Multiple Intestinal Neoplasia) allele of the mouse Apc gene develop numerous intestinal and colonic adenomas [on average 29±10, on a C57BL/6J (or equivalent derivative) background] that are similar in morphology to the adenomas seen in human inherited colonic polyposis syndromes such as familial adenomatous polyposis and Gardner's syndrome. Min/Min homozygotes die in utero. The Min mutation maps to mouse chromosome 18. The sequence of the Apc gene is known and published. Min mice carry a nonsense mutation in exon 15 of the mouse Apc gene (a mutation of the sort typically seen in human colon cancer kindreds). Mice carrying Min thus provide a model system for studying human familial adenomatous polyposis.

A locus (Mom-1) that strongly modifies the tumor number in heterozygous Min/+ mice was mapped to distal chromosome 4. Dietrich, W. F., et al., "Genetic Identification of Mom-1, a major modifier locus affecting Min-induced intestinal neoplasia in the mouse," *Cell* 75:631–639 (1993). Mom-1 lies in a region of synteny conservation with human chromosome 1p35-36, a region of frequent somatic loss of heterozygosity in a variety of human tumors, including colon tumors. Mom-1 is only one of an unknown number of loci that modify the expression of an inherited cancer syndrome, and it does not explain all of the genetic variation in tumor number in intraspecific backcrosses.

What is lacking is a systematic method for pinpointing genetic loci involved in modifying known phenotypes, by enhancing or suppressing. In the particular case of colon cancer in humans and animals, it would be desirable to locate the sequences in the genome (and the molecules encoded by those sequences) that are involved in the appearance of intestinal adenomas. The lack of such a systematic method has limited understanding of oncogenesis and, as such, has precluded development of pharmaceuticals that modify the oncogenic process. A systematic method should include not only non-essential loci, for which numerous mutant alleles can be found among homozygous inbred mouse strains, but also essential loci, for which mutant alleles in heterozygous form may influence the phenotype.

BRIEF SUMMARY OF THE INVENTION

The present invention permits detection of a genetic locus or loci that can modify a chosen known phenotype conferred by a chosen dominant allele. The method includes a mutagenic process that facilitates identifying and isolating the genetic sequences that encode the molecules that can modify the chosen phenotype, as well as the phenotype-modifying molecules themselves.

In the present method, mice are the non-human mammalian animals of choice, because of the synteny between humans and mice and because the genetics and breeding of mice are highly developed. Further, the mouse can exhibit disease phenotypes that are very similar to those of humans, as in the exemplified embodiment. The murine genetic sequences and the molecules obtained in the method are used to secure corresponding sequences and molecules from humans. The human sequences and molecules are then employed in known methods to develop pharmaceutical agents.

The breeding method includes the following steps. Each of a set of mice of a founder inbred mouse strain is outcrossed with a mouse of a second inbred mouse strain to obtain $F_1$ progeny. The animals of the founder mouse strain ("Generation 1" or "Gen1") carry random point mutations relative to wild-type mice of that strain. The second inbred mouse strain carries a dominant allele at a locus known to confer a chosen phenotype. The chosen phenotype is designated the "index phenotype." The index phenotype, which sensitizes the screening method to the phenotype of interest, is characterized in an index strain and provides a reference phenotype against which possible mutants can be compared. At least some of the Gen1 $F_1$ progeny carry both the dominant allele and at least one random mutation that may modify the index phenotype conferred by the dominant allele. A founder animal is judged to be of interest if a subset of its Gen1F$_1$ progeny are extensively modified for the index phenotype.

When a founder mouse has at least one Gen1F$_1$ offspring that displays a modified phenotype relative to control animals, the founder (Gen1) animal is crossed to an unmutagenized mouse of the founder strain to produce second generation (Gen2) offspring. Those offspring are again outcrossed to the index strain to obtain Gen2F$_1$ progeny. The presence of a phenotype-modifying mutation is then verified if a subset of the Gen2F$_1$ progeny are also modified for the index phenotype. Again, a cluster of animals with modified index phenotypes gives increasing confidence that the Gen1 founder carries a mutation of interest.

Genetic material that comprises the phenotype-modifying mutation can then be obtained using methods known to the art. Molecules encoded by the genetic material may also be obtained. The obtained genetic materials and molecules (or corresponding human equivalents) are used in methods known to the art to produce pharmaceutical agents that can ameliorate phenotypes noted in human or non-human patients affected in the biological process of interest.

It is an object of the present invention to provide a rapid, focused approach to obtaining genes in a model mammalian organism that can affect a biomedically-relevant phenotype.

It is an advantage of the present invention that the method can simultaneously identify an ensemble of several genes that can modify the index phenotype.

It is another advantage of the present invention that the method can uncover genes having no other known phenotype.

The present invention offers advantages over existing methods of obtaining genes, such as analysis of ESTs, in that genes secured in the present method are necessarily relevant to a biological phenotype. In contrast, genome-sequencing methods can provide voluminous sequence information for many genes, but offer little or no guidance as to the functional relationship among sequenced genes.

BRIEF DESCRIPTION OF THE FIGURE

FIG. 1 also depicts the survival times of individuals of four kindreds that exhibited progeny with longer or shorter survival times relative to the average survival time of Gen1F$_1$ mice carrying the index Min allele. Longer-surviving suppressor (Su) candidate kindreds 248 and 258 are shown as squares. Shorter-surviving enhancer (En) candidate kindreds 333 and 425 are shown as circles.

DETAILED DESCRIPTION OF THE INVENTION

Figure 1:
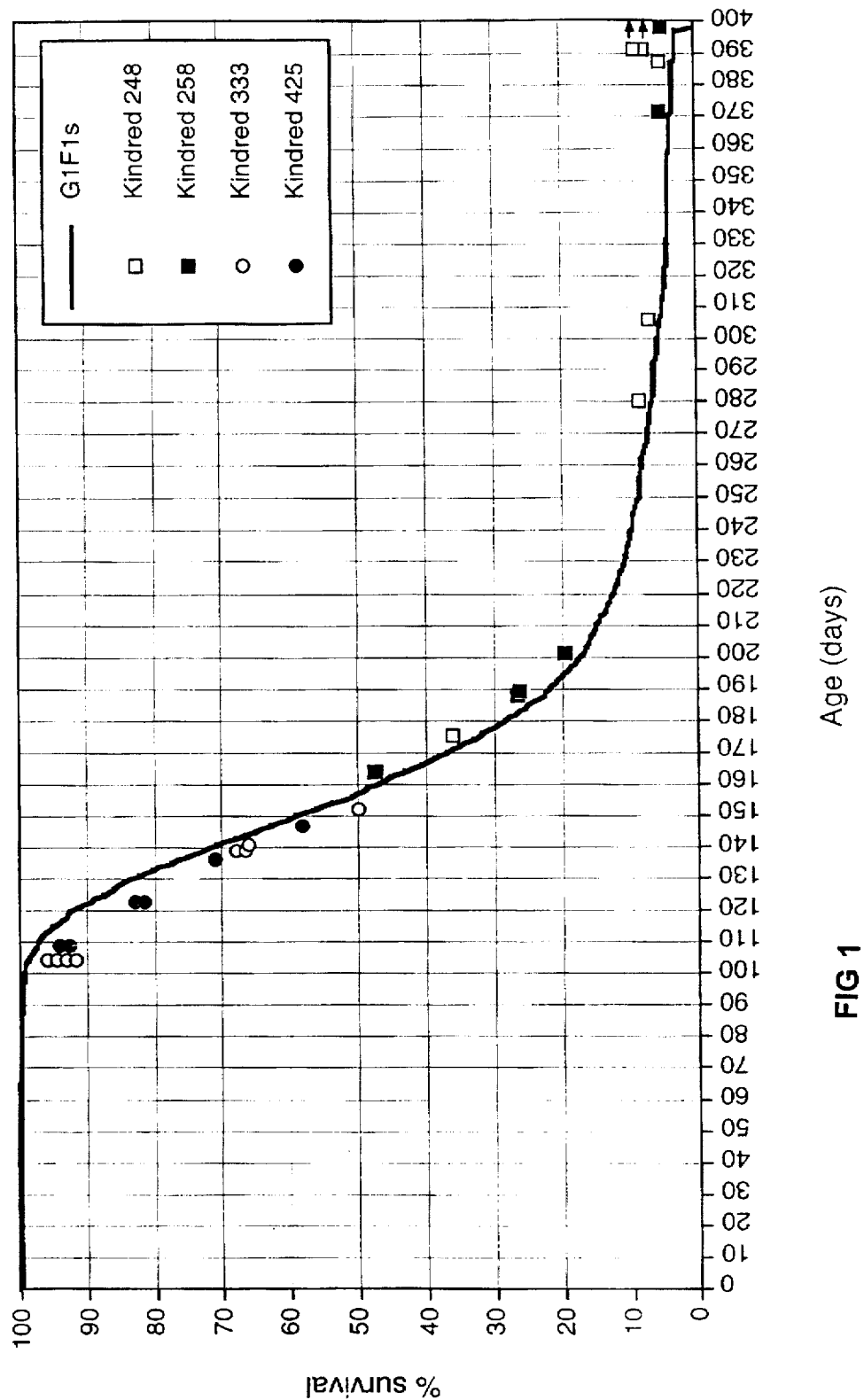
FIG. 1 depicts the probability of survival of Gen1F$_1$ mice bred in accordance with the method of the present invention.

A goal of the present invention is to identify genetic loci and genetic sequences that can modify a known phenotype. Although such analysis employing mutagenesis cannot be performed in humans for ethical reasons, the synteny and sequence conservation between human and mouse genomes provides a facile bridge to identify such loci and sequences in the human. It is likely that such sequences will correlate with existing human genetic sequence information. Thus, equivalent loci and genetic sequences can be sought in the human genome using conventional, available hybridization and PCR techniques.

The method is an Index-directed, Cluster-enhanced, Modifier locus and Molecule identification method that can be referred to as an "ICMM method."

The availability of inbred mice having a well defined genetic composition and well-studied phenotypes that model human syndromes, diseases, and other conditions, makes the mouse the preferred mammalian species in which to practice the present method. A preferred mouse species is *Mus musculus*.

The breeding system described herein is premised upon the existence of a phenotype that is evident in mice heterozygous for the allele that confers the chosen index phenotype. The index phenotype can be made "evident" by visual, biochemical, or other detection means. The phenotype-controlling allele can be lethal when present in the homozygous state. For cancer, the phenotype can relate either to effects that follow from the presence of an activated cancer-inducing allele or else from inactivation of a tumor suppressor gene that causes tumor formation in the absence of one normal copy of the gene. The phenotype can be governed by an allele on a sex chromosome or on an autosome. If the allele is on a sex chromosome, the breedings described herein are modified in a manner known to the art to ensure that the allele is maintained in the breeding pool.

The index phenotype is preferably conferred by a single dominant allele, although by taking care to produce suitable founder animals, phenotypes under the control of more than one locus can be studied in the method. It is not necessary that the phenotype-conferring allele is a defined genetic sequence, but rather the allele can be defined by classical genetic methods. It is advantageous that the allele is tightly linked to a genetic marker for genotype analysis, as is described elsewhere herein. With the dense microsatellite map of the mouse genome currently available, this condition is always met.

Phenotype-modifying loci are obtained in the present invention. A "modification" is any demonstrable change in an index phenotype relative to control animals lacking the phenotype-modifying allele, including, without limitation, enhancing or suppressing a phenotype, such as prolonging or shortening an animal's life span or circadian behavior. It is not necessary that the whole animal be affected by the modification. For example, a modified phenotype may be a change in a particular behavior or a change in the level of a particular biomolecule, such as a blood protein, after introducing a phenotype-modifying mutant allele in the method of the present invention. The assay for modified outliers in the first stage of the screen, Gen1F$_1$, will usually be relatively crude. One must judge whether an outlier is in the first or last 10 percentile range of the phenotypic distribution. For example, in a strain of mice having a well-defined running activity governed by a single dominant mutation (Clock)," the method described herein can be used to obtain animals having modified timing of that running activity. The genetic material (and protein molecules) responsible for that modification can be obtained by mapping and positionally cloning the modifying mutation.

The system is particularly amenable to study of genetic interactions in cancers known to have a genetic component. In particular, humans that carry an aberrant APC gene are predisposed to develop numerous tumors in the intestinal tract. Mice heterozygous for the Min allele of Apc, the murine homolog of human APC, also develop numerous tumors in the intestinal tract, similar to human inherited colonic polyposis syndromes. It is demonstrated herein that mutations induced in the genome elsewhere than at the Min locus can modify the survival rate and intestinal tumor load of mice carrying the Min gene.

Several important breeding considerations direct the selection of inbred mouse strains for use in the method. It is understood that those skilled in the art of mouse breeding are familiar with the breeding requirements of available mouse strains and such requirements need not be restated here.

The strain into which random mutations are introduced must be an inbred strain so that all modifications are the result of induced mutagenesis rather than genomic divergence. The strain should be susceptible to efficient germline mutagenesis. By "susceptible" the applicants intend that the strain have characteristic forward mutation rates of at least 1/500 per gamete per locus. In addition, the strain should have a long breeding span of at least one year. Also, it is preferred that the strain yield large litters, on average 8 or more pups per litter. A strain meeting these requirements is the inbred strain BTBR, which is commercially available from the Jackson Laboratory, Bar Harbor, Me. and elsewhere.

It is important that the inbred strain in which mutations are induced can be distinguished from the strain that contains the phenotype-conferring allele, e.g., by restriction fragment length polymorphisms (RFLP) or by simple sequence length polymorphisms (SSLP). A high incidence of informative differences in standard genetic markers between the two strains is important for mapping and cloning any mutation of interest. In one embodiment of the invention, the index phenotype (Min) was provided on a background of C57BL/6J (or equivalent derivative) (hereinafter, "B6-Min"). An "equivalent derivative" has an index phenotype comparable to that of B6-Min on a genuine C57BL/6J background. The BTBR strain used for mutagenesis in this embodiment is polymorphic at approximately half of the SSLP marker loci, relative to the B6 inbred strain.

It is also important that the two strains used in the method be relatively free of polymorphic dominant modifiers of the chosen index phenotype. By "relatively free" the applicants intend that differences in the index phenotype between Gen1F$_1$ animals and the index strain be sufficiently minor so as not to mask the effects of newly induced mutations. One skilled in the art will be able to determine the permissible variation for any given index phenotype. For example, in the case of the Min index phenotype, Gen1F$_1$ animals should show no more than about a 1.5-fold change in tumor multiplicity compared to B6-Min. In the Clock case, there should be no more than a 30 minute shift in circadian rhythm.

In the method, the strain that is to be mutagenized is treated with a mutagenic agent that induces mutations in the germline. It is important, for reasons associated with subsequent detection and isolation of mutants of interest, that the mutagen be an efficient point mutagen that can induce at least one mutation per locus per 500 gametes in the founder animal strain. Ethylnitrosourea (ENU) is a suitable and preferred mutagen which introduces almost exclusively point mutations in the mouse germline. A suitable protocol for ENU mutagenesis of mice is described in Shedlovsky et al., *Genet. Res., Camb.* 47:135–142 (1986), incorporated herein by reference. It is preferred, but not essential, that the mutagenesis be performed on male mice, since it is possible to obtain many offspring from a single mutagenized male. The mice are then crossed with unmutagenized mice of the same strain to produce isogenic animals, heterozygous only for the various mutations induced by the mutagenesis.

Each member of the set of Gen1 animals are crossed to mice heterozygous for the mutation conferring the index phenotype. It is desirable to produce up to 1000 of such Gen1 animals, to maximize the statistical likelihood that each of the approximately 1×10$^5$ genes in the mouse genome is examined at least once. If the mutation frequency is 1 per locus per 500 gametes, a 1000-member library of Gen1 animals would contain an average of 2 hits for each locus that can modify the index phenotype. The probability that a salient locus would escape attention would then be $e^{-2}$ or ≈10%. The cross can be done using Gen1 animals of either gender, unless the index phenotype compromises the successful breeding of one gender. It is sometimes possible to foster offspring when the female parent is compromised.

The kindreds are evaluated as follows. The phenotypic behaviors of the full set of Gen1F$_1$ animals are scored as are the phenotypes of individual kindreds. Where no modification is present, the behavior of individuals in the kindred would range over the average behavior of the full set. However, if a modifying mutation has been induced, and since the founder parent was heterozygous for the modifying mutation, on average 50% of the members of the kindred will show an outlying phenotype.

To improve the statistical likelihood that a modified phenotype is genuine, it is preferred that the modification be observed in two or more animals of a kindred having four or more members. A further condensation of the method is possible under these conditions. See, infra. It is most preferred that the kindred have at least six members and that three or more members are affected. It may be fruitful, however, to study smaller kindreds containing a single extreme outlier.

The female parents of kindreds that evidence possible modification by the above-noted standard are then crossed to unmutagenized mice of the same founder strain to maintain the mutation on a fixed background (a "copying generation"). The offspring of the copying generation are crossed again to mice heterozygous for the chosen phenotype to assess whether any of their offspring carry a bona fide modifying mutation. A genotypic analysis can be performed to determine which of these offspring carry the gene that confers the index phenotype. This can be particularly important when the phenotype is one that affects the lifespan of the Gen1 founder animals.

Mice shown by genotypic analysis to carry the index determinant are assessed as early as possible to determine whether any modification is apparent. If such a modified phenotype is observed, the specific genetic sequences responsible for the modification can be systematically identified using technology now available to the art. See, e.g., Zhang, Y. et al, "Positional cloning of the mouse obese gene and its human homologue," *Nature* 372:425–432 (1994), incorporated herein by reference, where murine coding sequences are identified on a contig (a continguous nucleic sequence of a portion of a chromosome determined by analyzing of a set of overlapping component nucleic acid sequences) constructed in the region of markers linked to a mutation. The murine coding sequences were identified by exon trapping (Church, D. M., et al, *Nature Genet.* 6:98–105 (1994), incorporated herein by reference), sequencing of trapped exons, comparing the sequences of trapped exons to all sequences in Genbank, screening putative exons for the presence of corresponding RNA in a variety of tissues by northern blots and reverse-transcription PCR. Then, by known methods of hybridization to human genetic material, the corresponding human gene was obtained. Alternatively, PCR primers prepared from the murine genetic sequences can be used to amplify corresponding human sequences from human genetic material. One skilled in the art can readily determine the similarity required between murine-derived primers and human target sequences in PCR methods.

The invention will be better understood upon consideration of the following non-limiting example.

EXAMPLE

The Min mutation, described by Moser et al., "A Dominant Mutation that Predisposes to Multiple Intestinal Neoplasia in the Mouse," *Science* 247:322-324 (1990), incorporated herein by reference, is a dominantly transmitted, fully penetrant mouse mutation that causes a phenotype in heterozygotes that closely resembles human inherited colonic polyposis syndromes. In this example, mice carrying the Min allele were bred with genetically-distinguishable BTBR mice that carried random point mutations inherited from mutagenized fathers.

At approximately 1 month intervals, 6 to 12 male BTBR mice were treated with ENU according to the protocol described by Shedlovsky, supra, and were then crossed to female, unmutagenized BTBR mice. The Gen1 offspring of that cross were isogenic BTBR heterozygotes for possible mutations that could affect the tumor load in mice that contain the Min mutation. Approximately 900 female Gen1 offspring were obtained over time.

Two hundred ninety-five Gen1 female mice were crossed with B6-Min male mice. As an aside, it is noted that multiple Gen1 males could have been crossed with B6-Min females, if the litters had been raised by foster mothers (such as ICR mice, commercially available) within a few days of birth. Over 90% of such pups survive. This strategy would be advantageous in that by providing multiple B6-Min females, production of a sufficient number of Gen1F$_1$ animals would be accelerated.

To perform the cross, two females and one male were placed in a cage. After two weeks, the females were withdrawn and replaced by two new females. Pregnancies were detected by weekly palpation of separated females. If no pregnancy was detected after two weeks of separation, the female was recycled into matings. The Gen1F$_1$ progeny from each female were genotyped for Min and were screened for signs of illness twice weekly starting at 100 days of age. When the animals began to look pale they were screened daily until they appeared close to death. The genotypic analysis employed allele-specific PCR or allele-specific hybridization, as described by Dietrich et al., supra, at page 637, and papers cited therein, all incorporated herein by reference, using the same PCR primers and conditions used by Dietrich et al.

Among the progeny were 92 kindreds having 6 or more members. Of these 92 kindreds, 5 kindreds showed at least two Min/+ members with possible enhancement of the Min phenotype (that is, a survival time shorter than the 90th percentile survival of the total population of Gen1F$_1$ mice). Seven kindreds showed at least two Min/+ members with suppression of the Min phenotype (that is, longer survival than the 10th percentile). As expected, the enhancement or suppression of the phenotype segregated within a kindred, since the Min mice in the Gen1F$_1$ generation are heterozygous for possible mutations.

The following table shows survival of four kindreds that include segregating candidate enhancer or suppressor loci:

| Kindred Number | Mouse Number | Born | Died | Last Age | % survival on Gen1F1 curve |
|---|---|---|---|---|---|
| Su248 | 1 | 10/20/yr1 | 11/11/yr2 | 388 | 2.9 |
| | 3 | 10/20/yr1 | 08/21/yr2 | 306 | 5.3 |
| | 2 | 10/20/yr1 | 07/26/yr2 | 280 | 6.6 |
| | 6 | 10/20/yr1 | 04/12/yr2 | 175 | 32.1 |
| Su258 | 4 | 10/11/yr1 | 11/12/yr2 | 398 | 0.0 |
| | 2 | 10/11/yr1 | 10/16/yr2 | 371 | 3.4 |
| | 14 | 02/14/yr2 | 09/30/yr2 | 229 | 11.0 |
| | 6 | 12/13/yr1 | 07/01/yr2 | 201 | 17.0 |
| | 7 | 12/13/yr1 | 06/19/yr2 | 189 | 22.4 |
| | 3 | 10/11/yr1 | 04/16/yr2 | 188 | 22.6 |
| | 11 | 12/13/yr1 | 05/25/yr2 | 164 | 43.3 |
| En333 | 15 | 03/06/yr2 | 08/05/yr2 | 152 | 56.1 |
| | 3 | 10/25/yr1 | 03/14/yr2 | 141 | 70.8 |
| | 12 | 03/06/yr2 | 07/23/yr2 | 139 | 72.7 |
| | 2 | 10/25/yr1 | 03/12/yr2 | 139 | 72.7 |
| | 13 | 03/06/yr2 | 06/18/yr2 | 104 | 98.7 |
| | 11 | 03/06/yr2 | 06/18/yr2 | 104 | 98.7 |
| | 10 | 03/06/yr2 | 06/18/yr2 | 104 | 98.7 |
| | 17 | 03/06/yr2 | 06/18/yr2 | 104 | 98.7 |
| En425 | 3 | 11/10/yr1 | 04/05/yr2 | 147 | 62.7 |
| | 1 | 11/10/yr1 | 03/25/yr2 | 136 | 76.4 |
| | 2 | 11/10/yr1 | 03/12/yr2 | 123 | 89.5 |
| | 6 | 11/10/yr1 | 03/12/yr2 | 123 | 89.5 |
| | 8 | 11/10/yr1 | 02/27/yr2 | 109 | 97.3 |
| | 6 | 11/10/yr1 | 02/27/yr2 | 109 | 97.3 |

If the probability is 10% that a mouse of normal genotype will survive longer than a particular age, the random probability that 2 mice in the same kindred will survive longer than that age is only 1%. The random probability that 3 mice in a kindred will survive longer is only 0.1%, in turn. Therefore, as the number of members of a kindred having an outlying short or long survival increases, so does the likelihood that the deviation results from a bona fide mutation inherited from the mutagenized BTBR founder animal. This is the cluster principle of the method. By predetermining a desired level of clustering, one can set limits on the ability to detect mutants and can raise the purification level of mutants obtained, thereby enriching the screen for mutants.

FIG. 1 depicts the probability of survival versus age in the Gen1F$_1$ generation of the cross between Gen1 BTBR females and B6-Min males. The symbols below and to the left of the curve reflect individuals in 2 kindreds thought to contain mutations that enhance the Min phenotype (En333 and En425). The symbols above and to the right of the curve reflect the members of 2 kindreds for whom the Min phenotype appears to be suppressed (Su248 and Su258). A number of the mice in the latter category remained alive at more than 365 days of age. Mice that showed statistically lower or higher survival were bred using standard methods to maintain the mutation. In some cases, the Gen1 animal failed to breed and the long term surviving Gen1F$_1$ mice were bred to the wild-type founder strain instead, as a fallback method for rescuing mutations of interest. For example, the founder parent of kindred Su258, described infra, was not able breed after a candidate mutation was identified in her progeny. Long-lived progeny animals number 2 and 4 were, therefore, bred to BTBR mice.

To verify that these outlying members of a kindred do indeed contain an enhancing or suppressing mutation, a second-generation kindred was examined. This is useful both to recover carriers of a strong enhancer mutation and to detect more subtle dominant affects of either the suppressor or the enhancer class. Commonly, heterozygotes for a loss of gene function show only a subtle heterozygous effect.

To produce the second generation kindred, the founder animal that gave rise to a kindred that evidenced either an enhancing or suppressing function was crossed to normal BTBR animals. On average, 50% of the offspring of this cross would be expected to contain the suppressing or enhancing mutation. The offspring of this cross, termed Gen2, were crossed to B6-Min mice.

After 90 days, the progeny shown by genotypic analysis to carry the Min mutation were sacrificed and tumor load was assessed using standard methods for determining average tumor volume and number. Tumor load is defined as average tumor volume times the number of tumors per mouse.

As further proof that a suppressing mutation was obtained in kindred 258, one of the long-term survivors in the Gen1F$_1$ generation was bred to B6-Min and a litter of offspring was obtained. Among the 3 Min/+ offspring, two had very low tumor counts (about 10 or fewer tumors) and a third had an average number of tumors (about 29 tumors). This provided strong evidence that a bona fide mutation having the effect of suppressing the Min phenotype was segregating upon passage to the offspring.

Because of the known SSLP polymorphisms between B6 and BTBR DNA, it will be possible to isolate the portion of the progeny genome that contains BTBR DNA and thereafter to localize the point mutation responsible for modifying the phenotype using standard techniques now available to the skilled molecular geneticist. The fact that ENU-induced mutations are single basepair substitutions makes this step particularly powerful. Thiss is the basis for the "Modifying Molecule" appellation of the ICMM method. The portion of the genome containing the point mutation can be compared against known ESTs, or can be sequenced de novo to determine the genetic sequence responsible for encoding the molecule that modifies the phenotype. Using standard methods, the genetic sequence can be introduced into a suitable genetic construct containing a transcriptional promoter for production in a prokaryotic or eukaryotic host cell. One could use the cloned gene to produce other mutations in this gene in companion mouse strains.

The genetic sequence is readily compared against known sequences from humans to determine the identity of the corresponding human gene. The human gene can be isolated by standard methods of hybridization, PCR, or expression cloning. The human protein can likewise be obtained using standard techniques, either by isolation from human tissue, or by production in a non-native host using recombinant DNA methods.

It may be possible to isolate mutations that suppress the index Min phenotype in a more compact, albeit less sensitive, method. In this method, B6-Min (heterozygous) female mice are crossed directly with ENU-mutagenized BTBR male mice. As a control, non-mutagenized BTBR male mice are also processed in the same way. The F$_1$ offspring are fostered on ICR mice. Male F$_1$ mice that have the Min phenotype are maintained.

At 170 days, any Apc$^{Min/+}$ F1 male whose body weight is greater than 95% of the control body weight is considered a candidate carrier of a dominant suppressor of the Min phenotype, Su/+.

Such candidate carriers are bred at 170 days of age to wild-type B6 female mice. The female offspring of this cross (Apc$^{Min/+}$ and Apc$^{+/+}$) are backcrossed to the candidate male who is by now only about 230 days old.

The progeny of the latter cross are then phenotyped at 90 days of age. By this time, the candidate male is at least 340 days old. Among the progeny, any detrimental or lethal phenotypes will inform about the map position of the suppressor and will indicate whether the candidate male carries a suppressor mutation.

| Apc$^{Min/+}$ Progeny: | |
|---|---|
| +/+ | normal Min phenotype |
| Su/+ | low tumor load at 90 days? |
| Su/Su | very low tumor load at 90 days? or detrimental or lethal? |
| Apc$^{+/+}$ Progeny: | |
| +/+ | normal |
| Su/+ | normal? |
| Su/Su | detrimental or lethal? |

Detrimentally affected animals will be homozygous for BTBR markers linked to the suppressor locus. By contrast, if Su/Su is an embryonic lethal mutation, the set of liveborn progeny will lack animals homozygous for BTBR markers linked to the suppressor locus.

It may also be important to rescue germplasm carrying a modifier mutation that enhances or suppresses, but particularly those that enhance, the Min phenotype, using in vitro fertilization. For example, a candidate carrier male who might be too sick to breed can be sacrificed. Sperm taken from the sacrificed male can be used to fertilize eggs obtained from a suitable female (e.g., BTBR or a mouse that carries the mutation of interest). The techniques that can be employed are described in Hogan, B. et al., *Manipulation of the Mouse Embryo*, Cold Spring Harbor Laboratory Press, 2nd. ed. (1994), incorporated herein by reference.

It is intended that the foregoing examples are non-limiting on the invention, but rather that the invention encompasses all such modifications and variations as come within the scope of the following claims.

We claim:

1. A method for identifying a segregating mutation at a murine genetic locus that modifies an index phenotype in an index inbred mouse strain, the segregating mutation causing an outlying phenotype relative to the index phenotype, the method comprising the steps of:

outcrossing a set of mice of a founder isogenic inbred mouse strain with a mouse of the index inbred mouse strain to obtain Gen1F$_1$ progeny, the founder isogenic inbred strain being heterozygous only for random point mutations relative to a wild-type mouse of the founder inbred strain, the index inbred mouse strain carrying a dominant allele at a locus known to confer the index phenotype, wherein at least some of the Gen1F$_1$ progeny carry both the dominant allele and at least one random mutation;

crossing a founder mouse of the founder isogenic inbred strain to a mouse of the founder strain that lacks the mutations to obtain inbred Gen2 offspring, wherein the founder mouse has at least one outcrossed F$_1$ progeny that displays the outlying phenotype relative to the index phenotype;

outcrossing Gen2 offspring to the index mouse strain to obtain Gen2F$_1$ backcross progeny, half of which, on average, carry the dominant allele that confers the index phenotype; and verifying that a subset of the Gen2F$_1$ progeny shows the outlying phenotype.

2. A method as claimed in claim 1 wherein the founder isogenic inbred mouse strain is produced by a method comprising the steps of:

treating a first wild-type mouse of the founder inbred strain with a mutagenic agent that induces point mutations;

crossing the treated mouse with a second wild-type mouse of the founder inbred strain to produce the founder isogenic inbred mouse strain heterozygous only for random point mutations.

3. A method as claimed in claim 2 wherein the mutagenic agent is ethylnitrosourea.

4. A method as claimed in claim 1 wherein the founder inbred mouse strain is BTBR.

5. A method as claimed in claim 1 wherein the index inbred mouse strain is C57BL/6J.

6. A method as claimed in claim 1 wherein the dominant allele at the locus known to confer the index phenotype is a Min allele at an Apc locus.

7. A method for identifying a human genetic sequence that corresponds to a segregating mutation at a murine genetic locus, the segregating mutation causing an outlying phenotype relative to an index phenotype in an index inbred mouse strain, the method comprising the steps of:

outcrossing a set of mice of a founder isogenic inbred mouse strain with a mouse of the index inbred mouse strain to obtain GenF$_1$ progeny, the founder isogenic inbred strain being heterozygous only for random point mutations relative to a wild-type mouse of the founder inbred strain, the index inbred mouse strain carrying a dominant allele at a locus known to confer the index phenotype, wherein at least some of the Gen1F$_1$ progeny carry both the dominant allele and at least one random mutation;

crossing a founder mouse of the founder isogenic inbred strain to a mouse of the founder strain that lacks the mutations to obtain inbred Gen2 offspring, wherein the founder mouse has at least one outcrossed F$_1$ progeny that displays the outlying phenotype relative to the index phenotype;

outcrossing Gen2 offspring to the index mouse strain to obtain Gen2F$_1$ backcross progeny, half of which, on average, carry the dominant allele that confers the index phenotype;

verifying that a subset of the Gen2F$_1$ progeny shows the outlying phenotype;

identifying genetic markers linked to the segregating mutation;

constructing a contig for the chromosomal region of the linked genetic markers;

identifying murine genes on the contig;

identifying a murine gene on the contig that encodes the segregating mutation; and recovering human genetic sequences corresponding to the mutation-encoding murine gene.

8. A method as claimed in claim 7 wherein the recovering step employs a method selected from the group consisting of hybridization and amplification.

9. A method for identifying a segregating mutation at a murine genetic locus that modifies an index phenotype of a Min allele at an Apc locus in a C57BL/6J mouse, the segregating mutation causing an outlying phenotype relative to the index phenotype, the method comprising the steps of:

outcrossing a set of isogenic BTBR strain founder mice heterozygous only for random point mutations relative to a wild-type BTBR mouse with a C57BL/6J mouse carrying the Min allele at the Apc locus to obtain GenF$_1$ progeny, wherein at least some of the Gen1F$_1$ progeny carry both the Min allele and at least one random mutation;

crossing a founder mouse of the isogenic BTBR strain to a wild-type BTBR mouse to obtain inbred Gen2 offspring, wherein the founder mouse has at least one outcrossed F$_1$ progeny that displays the outlying phenotype relative to the index Min phenotype;

outcrossing Gen2 offspring to C57BL/6J mice carrying the Min allele at the Apc locus to obtain Gen2F$_1$ backcross progeny, half of which, on average, carry the Min allele; and verifying that a subset of the Gen2F$_1$ progeny shows the outlying phenotype.

* * * * *